United States Patent
Lim et al.

(10) Patent No.: US 7,339,663 B2
(45) Date of Patent: Mar. 4, 2008

(54) METHOD AND APPARATUS FOR CLASSIFYING REPETITIVE DEFECTS ON A SUBSTRATE

(75) Inventors: Young-Kyu Lim, Gyeonggi-do (KR); Byung-Am Lee, Gyeonggi-do (KR); Byung-Seol Ahn, Gyeonggi-do (KR); Jae-Sun Cho, Gyeonggi-do (KR); Chang-Hoon Lee, Chungcheongnam-do (KR); Jung-Lan Lee, Busan (KR); Sung-Man Lee, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 320 days.

(21) Appl. No.: 11/181,162

(22) Filed: Jul. 13, 2005

(65) Prior Publication Data
US 2006/0012782 A1    Jan. 19, 2006

(30) Foreign Application Priority Data
Jul. 13, 2004    (KR) .................... 10-2004-0054346

(51) Int. Cl.
*G01N 21/00* (2006.01)
(52) U.S. Cl. ................ 356/237.5; 356/237.2; 382/144; 382/152
(58) Field of Classification Search .. 356/237.2–237.5; 382/144–152
See application file for complete search history.

(56) References Cited

U.S. PATENT DOCUMENTS

| | | | | |
|---|---|---|---|---|
| 6,466,895 B1 * | 10/2002 | Harvey et al. | | 702/181 |
| 6,876,445 B2 * | 4/2005 | Shibuya et al. | | 356/237.2 |
| 6,975,754 B2 * | 12/2005 | Hiroi et al. | | 382/149 |

FOREIGN PATENT DOCUMENTS

| | | |
|---|---|---|
| JP | 2004-117229 | 4/2004 |
| KR | 1999-49102 | 7/1999 |
| KR | 10-0286098 | 1/2001 |

OTHER PUBLICATIONS

English language abstract of the Korean Publication No. 1999-49102.
English language abstract of the Korean Publication No. 10-0286098, Oct. 1, 2001.
English language abstract of the Korean Publication No. 2004-117229.

* cited by examiner

*Primary Examiner*—Layla G. Lauchman
*Assistant Examiner*—Iyabo S Alli
(74) *Attorney, Agent, or Firm*—Marger Johnson & McCollom, P.C.

(57) ABSTRACT

A method and apparatus of classifying repetitive defects on a substrate is provided. Defects of dies on the substrate are sequentially compared with a predetermined reference die. Sets of coordinates are marked on the reference die which are corresponding to the position of the defects on the dies on the substrate. Then, repetitive defects are classified which are repeatedly marked in a specified region on the reference die.

25 Claims, 10 Drawing Sheets

METHOD AND APPARATUS FOR CLASSIFYING REPETITIVE DEFECTS ON A SUBSTRATE

CROSS REFERENCE TO RELATED APPLICATION

This application claims priority under 35 USC § 119 to Korean Patent Application No. 2004-54346, filed on Jul. 13, 2004, the contents of which are herein incorporated by reference in its entirety for all purposes.

BACKGROUND OF THE INVENTION

1. Field of the Invention

The present invention relates to a method and an apparatus for classifying repetitive defects on a substrate. More particularly, the present invention relates to an apparatus and method for classifying defects on dies of a substrate into repetitive defects and non-repetitive defects, and an apparatus for performing the method.

2. Description of the Related Art

Generally, a semiconductor device is manufactured under surroundings that include various contamination sources such as particles in air, contaminants generated from process equipment, reactants and/or products, etc. Thus, it is very difficult to find the contamination sources which provide defects in the semiconductor device, since hundreds of processes are performed in manufacturing a semiconductor device.

Meanwhile, the processes for manufacturing a semiconductor device include a photolithography process. According to the photolithography process, a pattern of a reticle is transcribed into a photoresist film over a semiconductor substrate using photolithography exposing equipment. The photolithography process includes an exposing process in which a light having a specific wavelength is irradiated onto the photoresist film through the reticle to expose the photoresist film, and a developing process in which a developing solution is provided to the exposed photoresist film to selectively remove the photoresist film. In this way, a photoresist pattern is formed on the semiconductor substrate. A layer on the semiconductor substrate is partially etched using the photoresist pattern as an etching mask to form a desired layer pattern on the semiconductor substrate.

Here, when the photolithography process is repeatedly performed using only one reticle, as shown in FIG. 1, particles generated from the photoresist film, etc., are continuously accumulated on the reticle. A light is reflected from the particles so that a path of the light is changed. Thus, as shown in FIG. 2, when the photoresist film is exposed using the reticle with accumulated particles thereon, defects such as a bridge are generated in the photoresist pattern.

Particularly, as shown in FIG. 3, when the exposing process is repeatedly carried out on dies positioned in a single shot region using the single reticle, the defects are repeatedly generated on substantially the same positions of the dies. For example, when the particles are attached to a ninth exposing portion of the reticle, the defects are repeatedly generated on each of the dies in the single shot region that is exposed by the ninth exposing portion of the reticle.

The repetitive defects are classified separately from all of the other defects on the semiconductor substrate so that the contamination of the reticle currently used is recognized. After the contamination of the reticle is recognized, the reticle is then cleaned or exchanged for new reticle. Therefore, to form a desired pattern on the semiconductor substrate, it is very important to classify the repetitive defects separately from all of the other defects on the photoresist pattern of each of the dies after performing the exposing process.

In a conventional method of classifying repetitive defects, a first die is sequentially compared with remaining dies. A second die is sequentially compared with the remaining the dies except the first die. A third die is sequentially compared with the remaining the dies except the first and second dies. This comparison is sequentially carried out on the all of the dies to classify repetitive defects separately from all of the other defects.

However, according to the conventional method, since any one die is compared with the remaining dies except previously compared dies, time for performing the conventional method is about 3 minutes to about 5 minutes. Thus, the time required for performing the conventional method is too long.

Also, for example, there is such a case that defects are repeatedly recognized on substantially same positions of each of first, second and third dies in a single shot region. However, the first, second and third dies are exposed by exposing portions of a reticle different from each other. Thus, the recognized defects do not correspond to repetitive defects.

However, in the conventional method, since the defects are not classified according to shot region, the recognized defects are mistakenly classified as the repetitive defects, and the normal reticle is determined to be abnormal. Due to this error, the normal reticle is cleaned or replaced with new reticle.

SUMMARY OF THE INVENTION

The present invention provides a method of classifying repetitive defects on a substrate in a relatively short time. The present invention also provides a method of classifying repetitive defects on a substrate that is capable of accurately classifying repetitive defects separately from all of the other defects on the substrate. The present invention still also provides an apparatus for performing the above-mentioned method.

A preferred method of classifying repetitive defects on a substrate is provided. The method comprises sequentially comparing defects of the dies on the substrate with a predetermined reference die. Sets of coordinates are marked on the reference die which are corresponding to the position of the defects on the dies on the substrate. Then, the step of classifying as the repetitive defects any defects which are repeatedly marked in a specified region on the reference die. Preferably, the method further comprises dividing the reference die into a plurality of classification regions that has a substantially square shape, wherein the specified region has a cross shape including the plurality of classification regions. The method can also preferably comprise the step of counting the number of the repetitive defects. Moreover, another step can preferably comprise displaying an alarm message, when the number of the repetitive defects is not less than a predetermined allowed number of repetitive defects.

Another preferred method of classifying repetitive defects on a substrate can also be provided. This method can comprise sequentially comparing defects of dies on the substrate with a predetermined reference die. Then, the substrate is divided into process regions wherein a process is performed. Next, sets of coordinates on the reference die are marked which are corresponding to the position of the defects on the dies on the substrate. Defects as preliminary repetitive defects are marked which correspond to coordinates which are repeatedly marked in a process region on the reference die. Whether the preliminary repetitive defects are positioned in substantially the same process region is determined. Finally, the preliminary repetitive defects within substantially the same process region as final repetitive defects are classified. The process regions preferably correspond to regions that are exposed using a reticle having exposing portions and which include the dies. The method further preferably comprises counting the total numbers of the repetitive defects on the substrate and the number of repetitive defects on each of the dies. Preferably, an alarm message is displayed when the total numbers of the repetitive defects on the substrate are not less than a predetermined allowed number of repetitive defects. More preferably, an alarm message is displayed when the total numbers of the repetitive defects on the substrate are not more than a predetermined allowed numbers set by the semiconductor, and the number of the repetitive defects on each of the dies are not less than the predetermined allowed number set by each of the dies. The method can also comprise dividing the reference die into a plurality of classification regions that have a substantially square shape, wherein the process region has a cross shape including a plurality of classification regions.

A further preferred method of classifying repetitive defects on a substrate can be provided. This method comprises sequentially comparing for defects process regions on the substrate with a predetermined reference process region. Sets of coordinates are marked on the reference process region corresponding to the positions of the defects on the process regions. Then, defects are classified on the reference process region corresponding to coordinates as repetitive defects which are repeatedly marked in a process region. Preferably, the process regions correspond to regions that are exposed using a reticle having exposing portions and including the dies. The method can further comprise dividing the reference process region into a plurality of classification regions that have a substantially square shape. The process regions can preferably have a cross shape including a plurality of classification regions.

The method can further comprise counting the number of repetitive defects. It can also preferably comprise displaying an alarm message when the numbers of the repetitive defects are not less than an allowed number of repetitive defects.

A preferred apparatus for classifying repetitive defects on a substrate can also be provided. The apparatus can comprise a die-comparing unit for sequentially comparing the dies on the substrate with a predetermined reference die, a coordinate-marking unit for marking sets of coordinates on the reference die which correspond to the position of the defects on the dies on the substrate, and a repetitive defect-classifying unit for classifying as repetitive defects, defects corresponding to coordinates which are repeatedly marked in a reference region provided on the reference die. The apparatus can further comprise a repetitive defect-counting unit for counting the number of the repetitive defects. It can also comprise an alarm unit for displaying an alarm message when the number of the repetitive defects are not less than a determined allowed number.

Another preferred apparatus for classifying repetitive defects on a substrate can be provided. This apparatus comprises a die-comparing unit for sequentially comparing the dies on the substrate with a predetermined reference die, the substrate being divided into process regions wherein a process is performed, a coordinate-marking unit for marking sets of coordinates on the reference die which correspond to the positions of all of the defects on the dies on the substrate, a process region-determining unit for determining whether preliminary repetitive defects are positioned in a substantially same process region, and a repetitive defect-classifying unit for preliminarily classifying defects corresponding to coordinates, which are marked in a reference region on the reference die as preliminary repetitive defects, and for finally classifying the preliminary repetitive defects as final repetitive defects in accordance with a determination by the process region-determining unit. Preferably, a repetitive defect-counting unit is provided for counting the total number of the repetitive defects on the substrate and the number of repetitive defects on each of the dies. The apparatus preferably further comprises an alarm unit for displaying an alarm message when the total number of the repetitive defects on the substrate are not less than allowed numbers, or when the total number of the repetitive defects on the substrate are not more than allowed numbers set by the semiconductor, and the numbers of the repetitive defects on each of the dies are not less than the predetermined allowed numbers set by each of the dies.

A further preferred apparatus for classifying repetitive defects on a substrate comprises a process region-comparing unit for sequentially comparing the process regions on the substrate with a predetermined reference process region, a coordinate-marking unit for marking coordinates on the reference process region which corresponds to the position of the defects on the process regions, and a repetitive defect-classifying unit for classifying defects as repetitive defects corresponding to coordinates which are repeatedly marked in a process region on the reference process region.

BRIEF DESCRIPTION OF THE DRAWINGS

The above and other features and advantages of the invention will become readily apparent by reference to the following detailed description when considered in conjunction with the accompanying drawings wherein.

DESCRIPTION OF THE EMBODIMENTS

Figure 1:
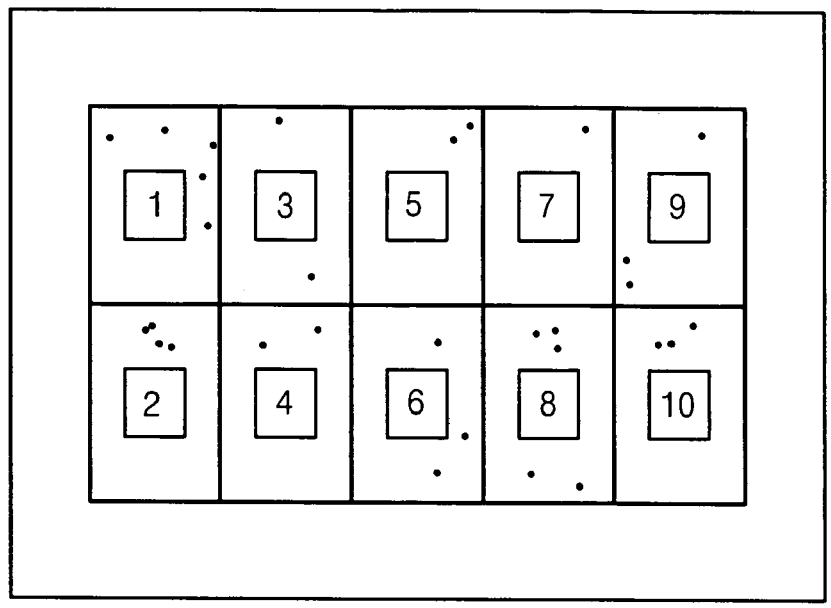
FIG. 1 is a plan view illustrating a reticle to which particles are attached.
Figure 2:
FIG. 2 is a scanning electron microscope (SEM) picture illustrating a photoresist pattern formed by an exposing process using the reticle in FIG. 1.
Figure 3:
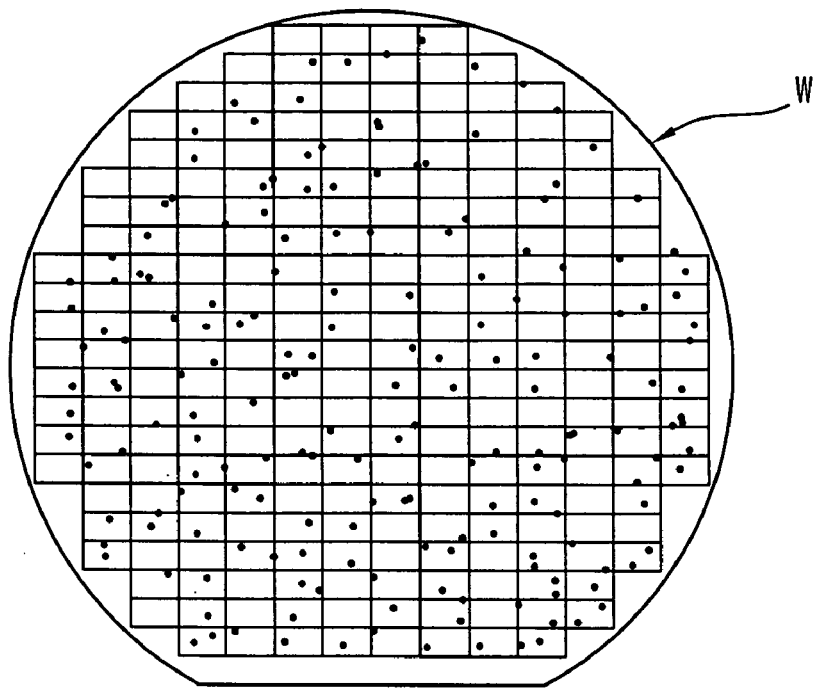
FIG. 3 is a plan view illustrating a substrate map prepared by a conventional method.

The present invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or a layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Embodiment 1

Figure 4:
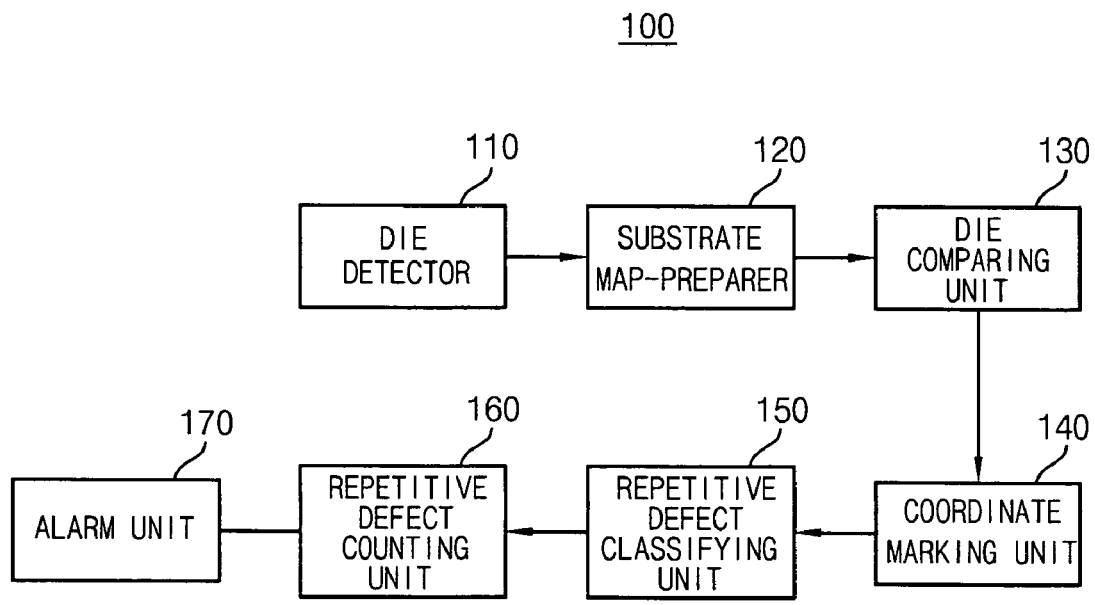
FIG. 4 is a block diagram illustrating an apparatus for classifying repetitive defects in accordance with a first embodiment of the present invention.

Referring to FIG. 4, an apparatus 100 for classifying repetitive defects in accordance with the present embodiment receives information from a defect-detecting unit. The defect-detecting unit includes a defect detector 110 for detecting all of the defects on a semiconductor substrate and a map preparer 120 for preparing a map of the semiconductor substrate on which positions of all of the defects detected by the defect detector 110 are marked.

Figure 5:
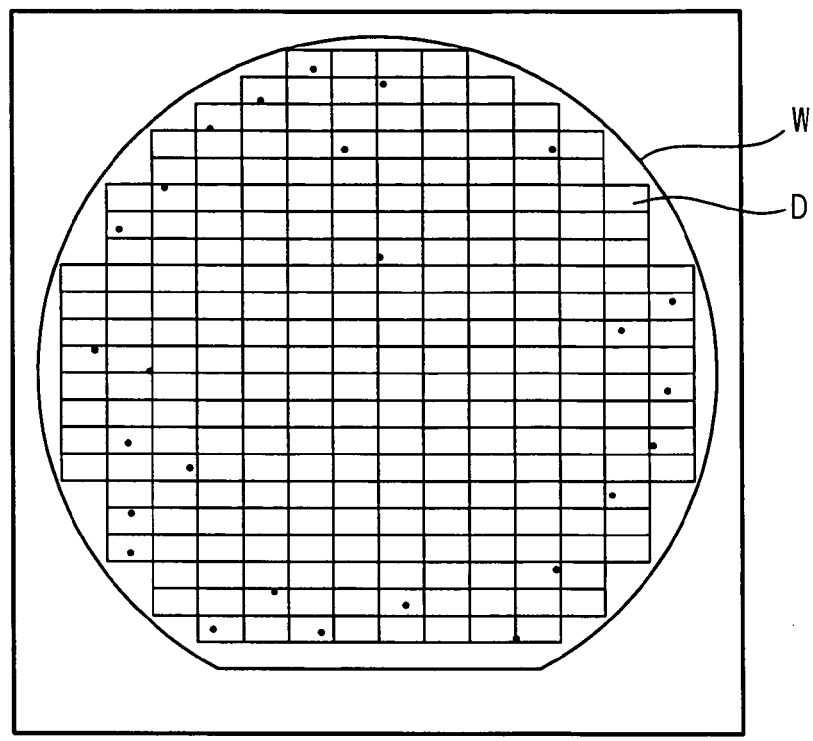
FIG. 5 is a plan view illustrating a substrate map prepared by a map-preparing unit of the apparatus in FIG. 4.

Referring to FIG. 5, the map preparer 120 prepares the substrate map on which the positions of all of the defects are marked. Here, the semiconductor substrate W is divided into a plurality of dies D. The substrate map is provided to the classifying apparatus 100.

Referring now to FIG. 4, the classifying apparatus 100 includes a die-comparing unit 130 for comparing the dies D on the substrate map with a reference die, a coordinate-marking unit 140 for marking the positions of all of the defects on the reference die, and a repetitive defect-classifying unit 150 for classifying repetitive defects separately from all of the other defects.

Additionally, the classifying apparatus 100 may further include a repetitive defect-counting unit 160, and an alarm unit 170 for displaying an alarm message in accordance with the result of the count by the repetitive defect-counting unit 160.

Figure 6:
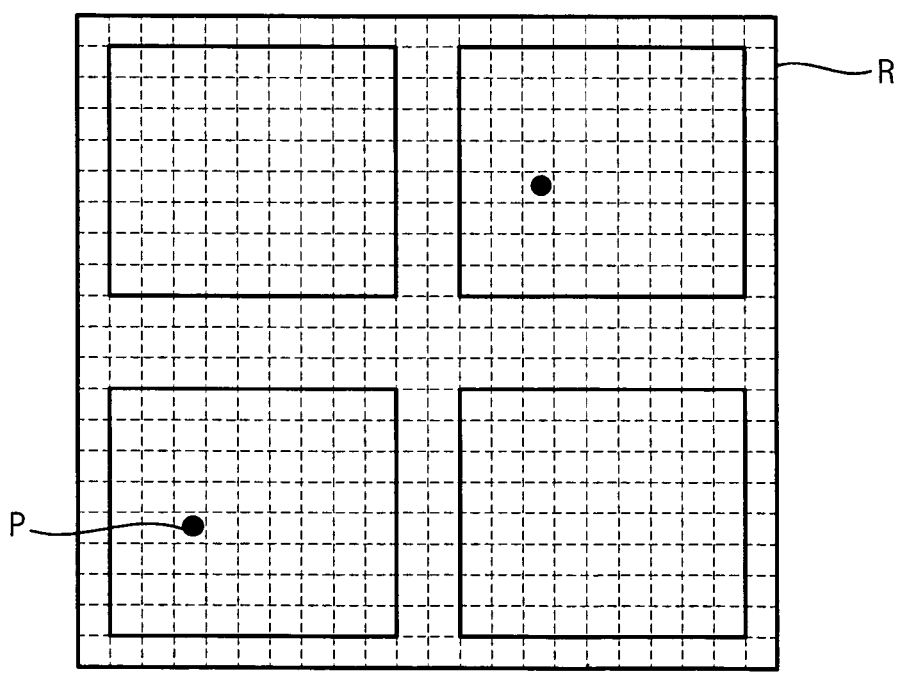
FIG. 6 is a plan view illustrating a reference die.

The die-comparing unit 130 receives the substrate map from the map-preparing unit 120. Meanwhile, as shown in FIG. 6, the reference die R is set up in the die-comparing unit 130. The reference die R has a size substantially identical to that of each of the dies D on the substrate map. Also, an X-Y coordinate system is set up on the reference die R. Thus, virtual lines are drawn on the reference die R in an X direction and in a Y direction, respectively, so that the reference die R is divided into a plurality of square classification regions having substantially same areas. In the present embodiment, each of the classification regions has an area of about 2.5 µm X about 2.5 µm.

The die-comparing unit 130 compares a first die D1 in FIG. 6 with the reference die R. The die-comparing unit 130 then compares a second die D2 with the reference die R. The die-comparing unit 130 sequentially compares the remaining dies D, except for the first and second dies D1 and D2, with the reference die R.

The coordinate-marking unit 140 marks the positions of all of the defects on all of the dies D on the reference die R. Thus, the positions of all of the defects on all of the dies D are marked on the reference die R. Therefore, when the defects are repeatedly marked in any one of the classification regions of the reference die R, the repetitive defect-classifying unit 150 classifies the repeatedly marked defects as the repetitive defects.

Figure 7:
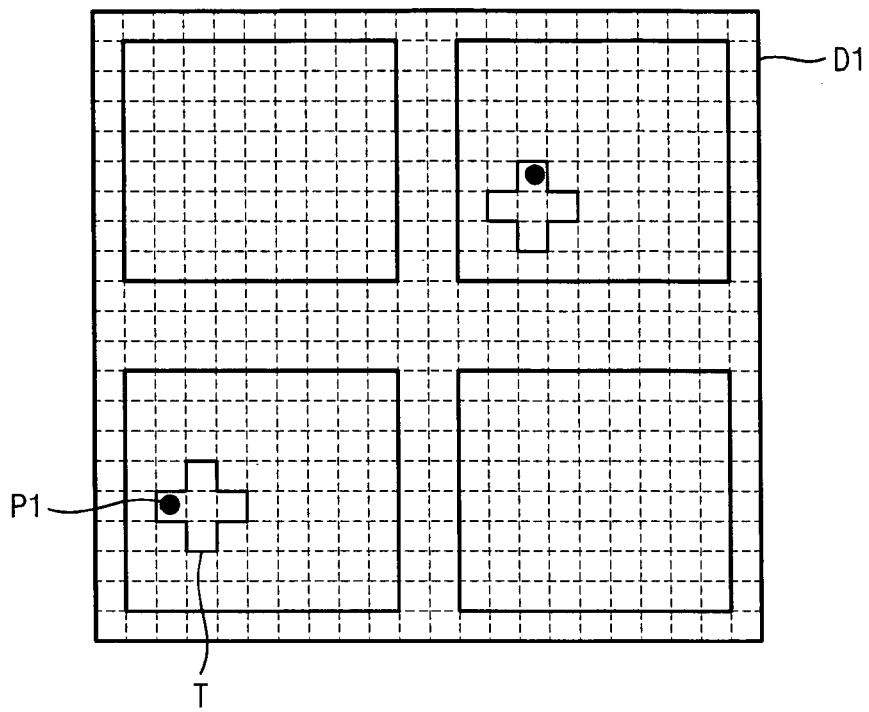
FIGS. 7 and 8 are plan views illustrating first and second dies on the substrate map in FIG. 5.
Figure 8:
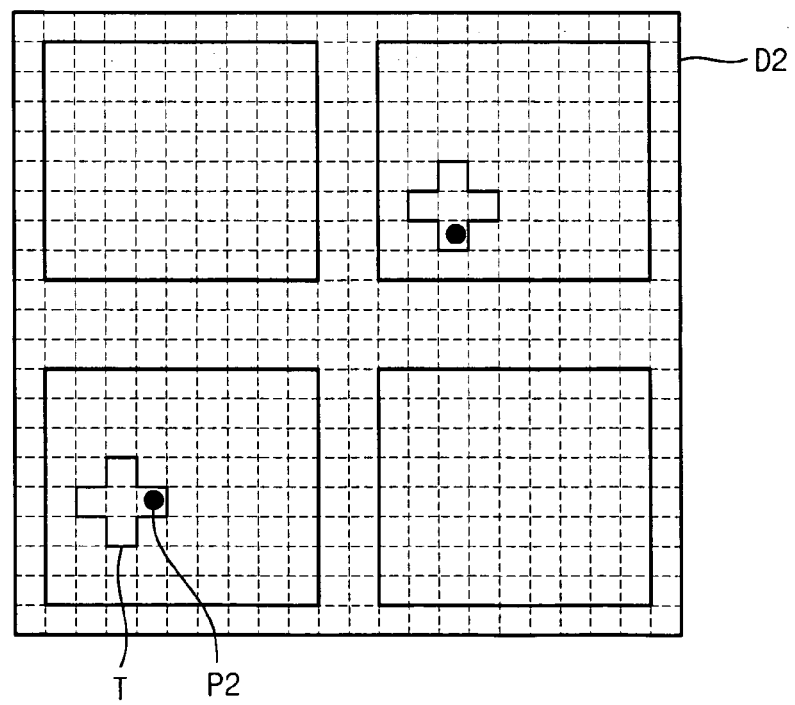

Here, the defects may not be positioned on a substantially same position in each of the dies D. To classify these defects as the repetitive defects, as shown in FIGS. 7 and 8, a tolerance region T having a cross shape that includes five classification regions is set up on each of the dies D. Although a first defect P1 on the first die D1 in FIG. 7 and a second defect P2 on the second die D2 in FIG. 8 are positioned in different classification regions, the first and second defects P1 and P2 are positioned in the tolerance region T. Thus, the coordinate-marking unit 140 marks the first and second defects P1 and P2 on one point P in the reference die R. As a result, the repetitive-classifying unit 150 finally classifies the first and second defects P1 and P2 as the repetitive defects.

The repetitive defect-counting unit 160 counts the finally classified repetitive defects. Also, the repetitive defect-counting unit 160 determines whether the numbers of the counted repetitive defects are no less than allowed numbers of the repetitive defects or not. Here, the allowed numbers are set up for determining a reticle to be normal or abnormal.

That is, when the numbers of the counted repetitive defects are not less than the allowed numbers, the reticle is determined to be abnormal, and vice versa.

When the numbers of the counted repetitive defects are not less than the allowed numbers, the alarm unit 160 displays the alarm message so that a worker recognizes the reticle to be abnormal. As a result, the worker cleans the reticle to remove the repetitive defects from the reticle or exchanges the reticle for new one.

Figure 9:
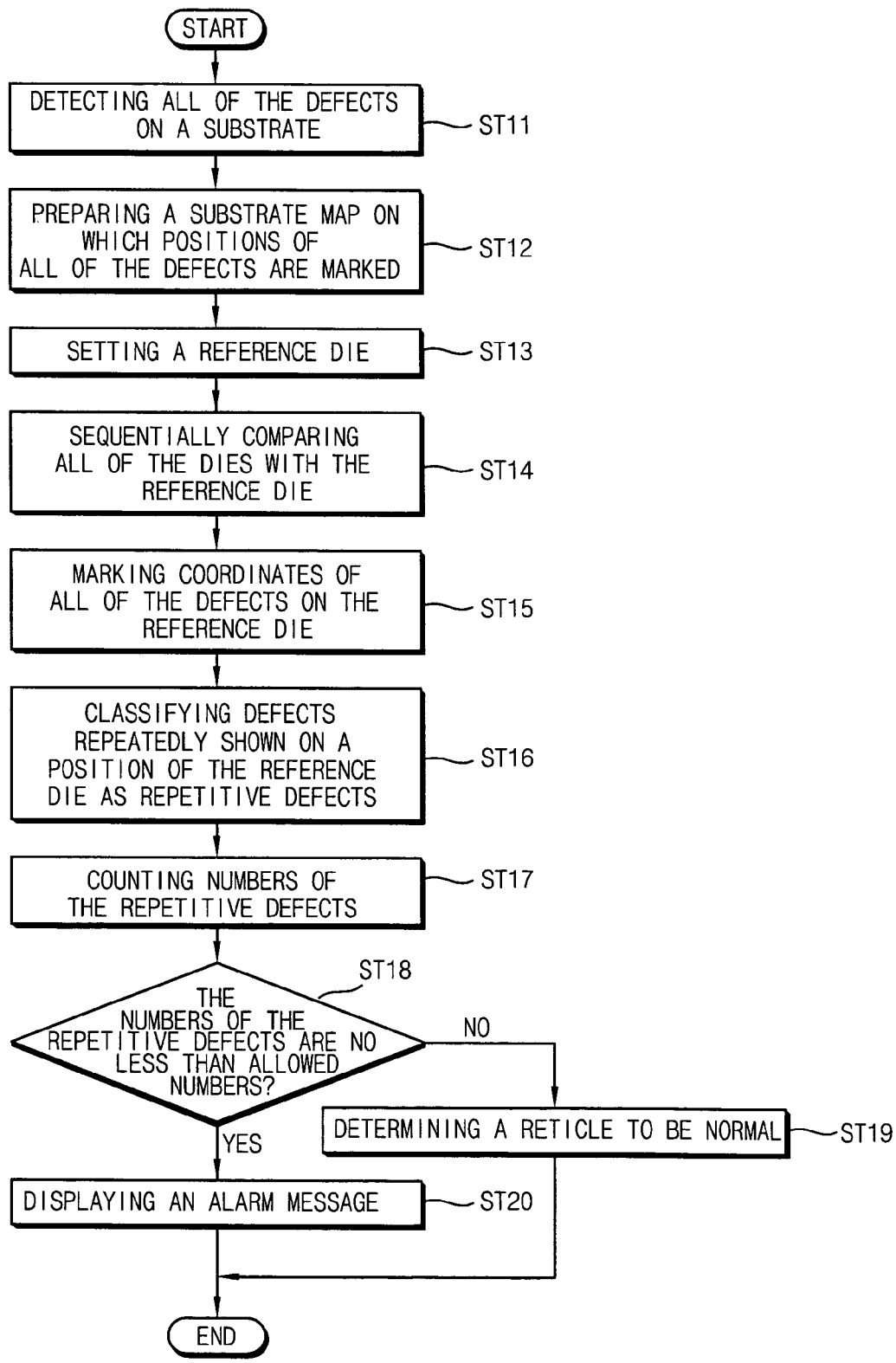
FIG. 9 is a flow chart illustrating a method of classifying repetitive defects using the apparatus in FIG. 4.

FIG. 9 is a flow chart illustrating a method of classifying repetitive defects using the apparatus in FIG. 4.

First of all, any one of processes for manufacturing a semiconductor device can be performed on each of the dies of the semiconductor substrate. An example of the process includes an exposing process. In the exposing process, a light is irradiated onto a photoresist film on the semiconductor substrate through a reticle to form a photoresist pattern. In particular, the reticle has only one exposing portion so that the exposing process is carried out on single die.

Referring to FIGS. 4 and 9, in step ST11, after the exposing process is completed, the defect detector 110 detects all of the defects D on the semiconductor substrate W. The method of detecting all of the defects D may be classified into a method using an image and a method using a light signal profile.

In the method using the image, a light is irradiated onto the semiconductor substrate W. The image is obtained from a light reflected from the semiconductor substrate W. The obtained image is compared with a predetermined reference image to detect all of the defects D.

In the method using the light signal profile, a light is irradiated onto the semiconductor substrate W. The light signal profile is obtained from a light scattered from the semiconductor substrate W. The obtained light signal profile is compared with a predetermined reference light signal profile to detect all of the defects D.

In the present embodiment, all of the defects D on the semiconductor substrate W may be detected using any one of the above-mentioned methods.

In step ST12, the map preparer 120 prepares the substrate map on which all of the defects D are marked. The substrate map is divided into a plurality of the dies D.

In step ST13, the reference die R without defects is set up in the die-comparing unit 130. The reference die R has a size substantially identical to that of the die D on the substrate map. Also, the X-Y coordinate system is set up on the reference die R.

In step ST14, the die-comparing unit 130 sequentially compares each of the dies D on the substrate map with the reference die R. In particular, the die-comparing unit 130 compares the first die D1 with the reference die R. The die-comparing unit 130 then compares the second die D2 with the reference die R. The die-comparing unit 130 sequentially compares the remaining dies D with the reference die R. For example, when each of the dies D is overlapped with the reference die R, the defects on each of the dies D are shown on the reference die R. Thus, the positions of all of the defects are shown on the X-Y coordinate system of the reference die R.

In step ST15, after all of the dies D are compared with the reference die R, the coordinate-marking unit 140 marks the positions of all of the defects on the X-Y coordinate system of the reference die R. As a result, the positions of all of the defects are shown on the reference die R.

In step ST16, the repetitive defects among all of the defects are repeatedly marked on a substantially same position of the X-Y coordinate system. Here, the repetitive defects may not be accurately positioned at the same position. Therefore, the tolerance region for defining a boundary where the defects are classified into the repetitive defects is set up from a position on the X-Y coordinate system. For example, a region positioned within predetermined lengths from the position in the X-direction and the Y-direction is set up as the tolerance region. The repetitive defect-classifying unit 150 classifies the defects repeatedly shown in the tolerance region as the repetitive defects.

In step ST17, the repetitive defect-counting unit 160 counts the numbers of the repetitive defects.

In step ST18, the repetitive defect-counting unit 160 determines whether the numbers of the repetitive defects are no less than the allowed numbers or not.

In step ST19, when the numbers of the repetitive defects are no more than the allowed numbers, the reticle is determined to be normal.

On the contrary, in step ST20, when the numbers of the repetitive defects are no less than, i.e., more than, the allowed numbers, the alarm unit 170 displays the alarm message so that the worker recognizes the reticle to be abnormal.

Here, the alarm message may have a function for informing the worker of the existence of the repetitive defects. Alternatively, the alarm message may have an additional function for preventing a subsequent process from being performed in order for the worker to manage the repetitive defects.

According to the present embodiment, since all of the dies in the substrate map are compared with the reference die, the time required for classifying the repetitive defects may be from about 30 seconds to about 60 seconds. As a result, the time required for classifying the repetitive defects may be substantially reduced compared to that of the conventional method.

Embodiment 2

Figure 10:
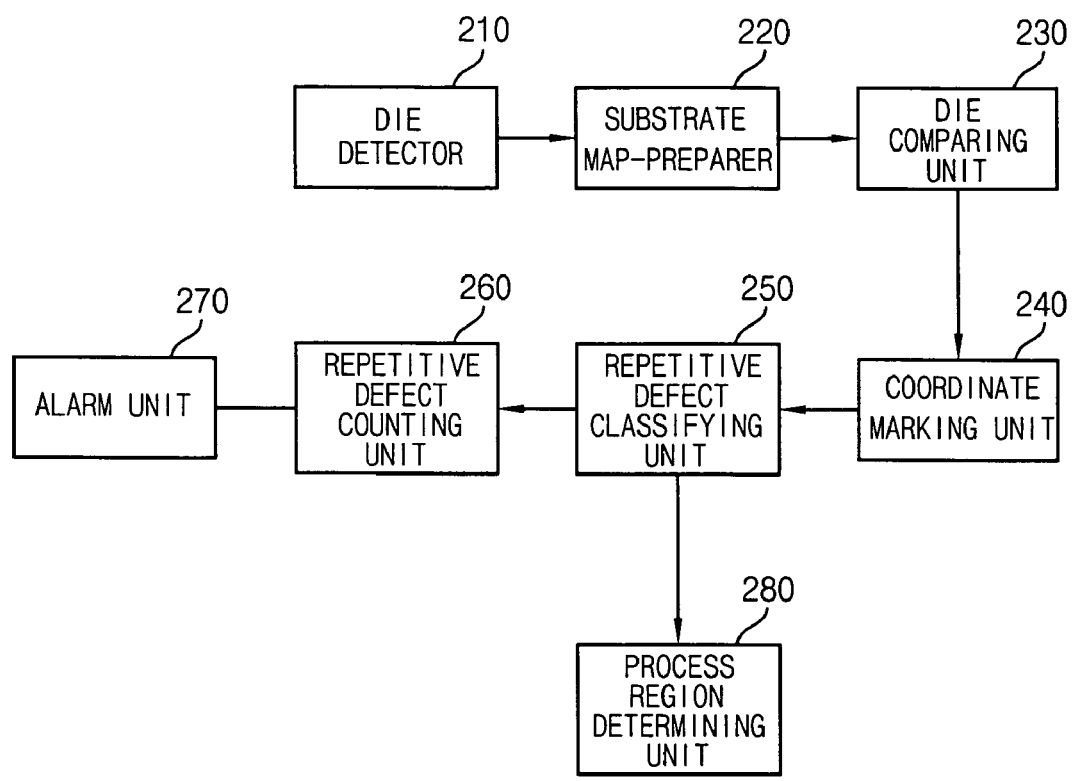
FIG. 10 is a block diagram illustrating an apparatus for classifying repetitive defects in accordance with a second embodiment of the present invention.

Referring to FIG. 10, an apparatus 200 for classifying repetitive defects in accordance with the present embodiment includes a defect detector 210 for detecting all of the defects on a semiconductor substrate and a map preparer 220 for preparing a map of the semiconductor substrate on which positions of all of the defects detected by the defect detector 210 are marked.

Figure 11:
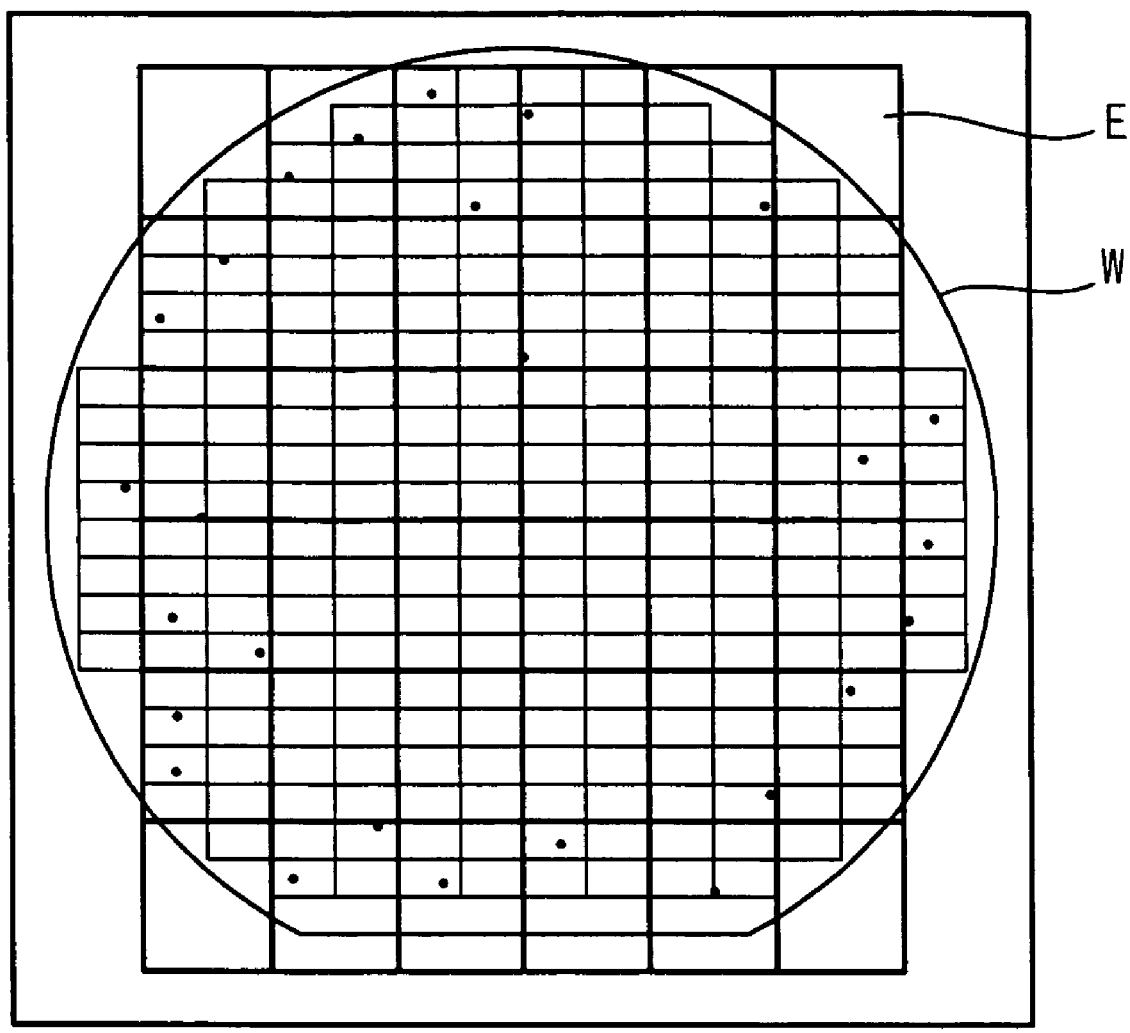
FIG. 11 is a plan view illustrating a substrate map prepared by a map-preparing unit of the apparatus in FIG. 10.

Referring to FIG. 11, the map preparer 220 prepares the substrate map on which the positions of all of the defects are marked. Here, the semiconductor substrate W is divided into a plurality of process regions E. Each of the process regions includes a plurality of dies D. The substrate map is provided to the classifying apparatus 200.

Referring now to FIG. 10, the classifying apparatus 200 includes a die-comparing unit 230 for comparing the dies D on the substrate map with a reference die, a coordinate-marking unit 240 for marking the positions of all of the defects on the reference die, a process region-determining unit 280 for determining the positions of the process regions E in which the defects exist, and a repetitive defect-classifying unit 250 for classifying repetitive defects from all of the defects.

Additionally, the classifying apparatus 200 may further include a repetitive defect-counting unit 260 for counting the numbers of all of the defects and the numbers of the defects in each of the dies D, and an alarm unit 270 for displaying an alarm message in accordance with the result of the count by the repetitive defect-counting unit 260.

The die-comparing unit 230 and the coordinate-marking unit 240 are substantially identical to those in Embodiment 1, respectively. Thus, any further illustrations of the die-comparing unit 230 and the coordinate-marking unit 240 are omitted.

The process region-determining unit 280 determines the positions of the process regions E in which the defects compared with the reference die exist. In particular, each process region E includes twelve dies. The die-comparing unit 230 sequentially compares the twelve dies D with the reference die. When a thirteenth die is compared with the reference die, the process region-determining unit 280 determines the thirteenth die as a die included in another process region.

The repetitive defect-classifying unit 250 classifies defects repeatedly marked in the tolerance region of the reference die as preliminary repetitive defects. The repetitive defect-classifying unit 250 receives information, which includes whether the preliminary repetitive defects are positioned in a same process region, or not, from the process region-determining unit 280. When the preliminary repetitive defects are positioned in the same process region, the repetitive defect-classifying unit 250 finally classifies the preliminary repetitive defects as non-repetitive defects. On the contrary, when the preliminary repetitive defects are positioned in a process region different from each other, the repetitive defect-classifying unit 250 finally classifies the preliminary repetitive defects as the repetitive defects.

The repetitive defect-counting unit 260 counts total numbers of the finally classified repetitive defects on the semiconductor substrate. Also, the repetitive defect-counting unit 260 counts each of the numbers of the finally classified repetitive defects by each of the dies.

When the total numbers of the counted repetitive defects are not less than, i.e., more than, the allowed numbers, the alarm unit 270 displays the alarm message. Also, when the total numbers of the counted repetitive defects are not more than the allowed numbers, and each of the numbers of the counted repetitive defects by each of the dies are not less than the allowed numbers, the alarm unit 270 displays the alarm message.

Figure 12:
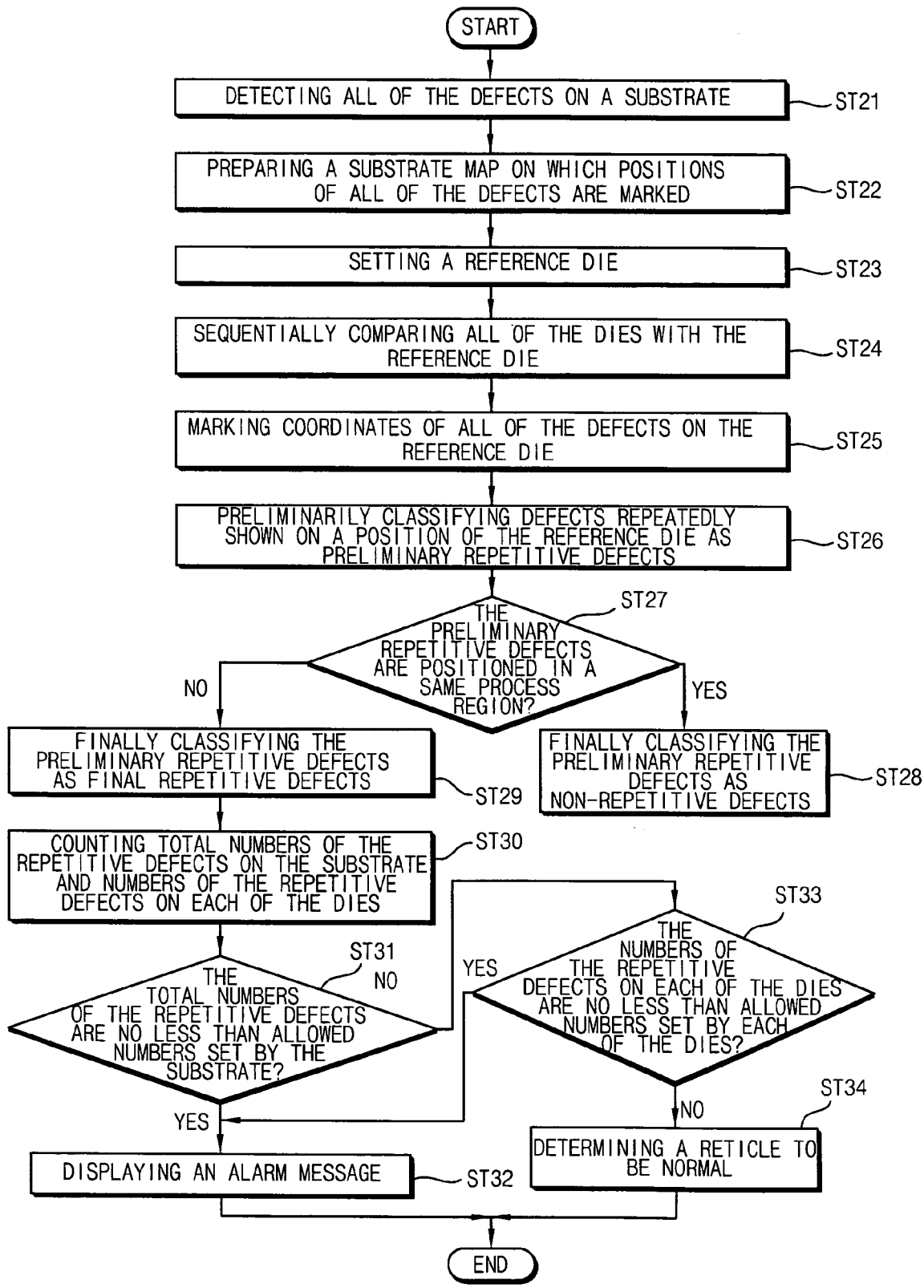
FIG. 12 is a flow chart illustrating a method of classifying repetitive defects using the apparatus in FIG. 10.

FIG. 12 is a flow chart illustrating a method of classifying repetitive defects using the apparatus in FIG. 10.

First of all, any one of the processes for manufacturing a semiconductor device is performed on each of the dies of the semiconductor substrate. An example of the process includes an exposing process. In the exposing process, a light is irradiated onto a photoresist film on the semiconductor substrate through a reticle to form a photoresist pattern. In particular, the reticle has twelve exposing portions so that the exposing process is carried out on the process region including twelve dies. Thus, since all of the dies are divided into forty-eight process regions, forty-eight exposing processes are performed.

Referring to FIGS. 10 and 12, in step ST21, the defect detector 210 detects all of the defects on the semiconductor substrate.

In step ST22, the map preparer 220 prepares the substrate map on which all of the defects are marked. The substrate map is divided into a plurality of dies. Also, each of the forty-eight process regions including the twelve dies is set on the substrate map. Each of the process regions corresponds to each of the exposing portions, respectively.

In step ST23, the reference die without defects is set up in the die-comparing unit 230. The reference die corresponds to the process regions.

In step ST24, the die-comparing unit 230 sequentially compares each of the dies on the substrate map with the reference die.

In step ST25, the coordinate-marking unit 240 marks the positions of all of the defects on the X-Y coordinate system of the reference die.

In step ST26, the repetitive defect-classifying unit 250 classifies defects repeatedly marked in the tolerance region that are set from a position on the X-Y coordinate system of the reference die as preliminary repetitive defects.

In step ST27, the process region-determining unit 280 determines whether the preliminary repetitive defects are positioned in the same process region or not. That is, the process region-determining unit 280 recognizes whether the preliminary repetitive defects are included in single shot region.

In step ST28, when the preliminary repetitive defects are positioned in the same process region, the repetitive defect-classifying unit 250 finally classifies the preliminary repetitive defects as the non-repetitive defects. In particular, the preliminary repetitive defects are repeatedly shown in the tolerance region of the reference die. However, the preliminary repetitive defects are positioned in the dies included in the single shot region. The dies in the single shot region are exposed through the exposing portions of the reticle different from each other. Thus, although the preliminary repetitive defects are repeatedly shown in the tolerance region, the preliminary repetitive defects are not caused from a same exposing portion. For example, one defect is caused from a first exposing portion of the reticle. On the contrary, another defect is caused from a second exposing portion of the reticle. These defects are repeatedly shown in the tolerance region of the reference die. Therefore, the preliminary repetitive defects in the same process region are classified as the non-repetitive defects.

On the contrary, in step ST29, when the preliminary repetitive defects are not positioned in the same process region, the repetitive defect-classifying unit 250 finally classifies the preliminary repetitive defects as the final repetitive defects. The preliminary repetitive defects in the process regions different from each other are caused from a same exposing portion of the reticle. Thus, when the preliminary repetitive defects are positioned in the process regions different from each other, the preliminary repetitive defects are classified as the final repetitive defects.

In step ST30, the repetitive defect-counting unit 260 counts the total numbers of the repetitive defects on the semiconductor substrate. Also, the repetitive defect-counting unit 260 counts the numbers of the repetitive defects on each of the dies. For example, when a great number of particles are attached to one exposing portion and a small number of particles are attached to another exposing portion, the repetitive defects are concentratedly generated in any one of the dies. The total numbers of the repetitive defects are no more than the allowed numbers so that the reticle may be determined to be normal. However, since the reticle has the exposing portion to which a great number of particles are attached, numerous defects may be generated in the dies exposed with the exposing portion.

In step ST31, the repetitive defect-counting unit 260 determines whether the total numbers of the repetitive defects are not less than the allowed numbers by the semiconductor substrate or not.

In step ST32, when the total numbers of the repetitive defects are not less than the allowed numbers by the semiconductor substrate, the alarm unit 270 displays the alarm message so that the worker recognizes the reticle to be abnormal.

On the contrary, in step ST33, when the total numbers of the repetitive defects are not more than the allowed numbers of the semiconductor substrate, the repetitive defect-counting unit 260 determines whether the numbers of the repetitive defects on each of the dies are not less than the allowed numbers by each of the dies or not. Here, determining the numbers of the repetitive defects on each of the dies may be carried out on only one die to which the most repetitive defects are attached.

In step ST32, when the numbers of the repetitive defects on each of the dies are not less than the allowed numbers by each of the dies, the alarm unit 270 displays the alarm message. Here, the alarm message may have a function for informing the worker of the existence of the repetitive defects. Alternatively, the alarm message may have an additional function for preventing a following process from being performed in order for the worker to manage the repetitive defects.

In step ST34, when the numbers of the repetitive defects on each of the dies are not more than the allowed numbers by each of the dies, the reticle is determined to be normal.

According to the present embodiment, since each of the dies is compared with the reference die and is also recognized whether each of the dies are positioned in the same process region, the repetitive defects may be accurately classified in a short time.

Embodiment 3

Figure 13:
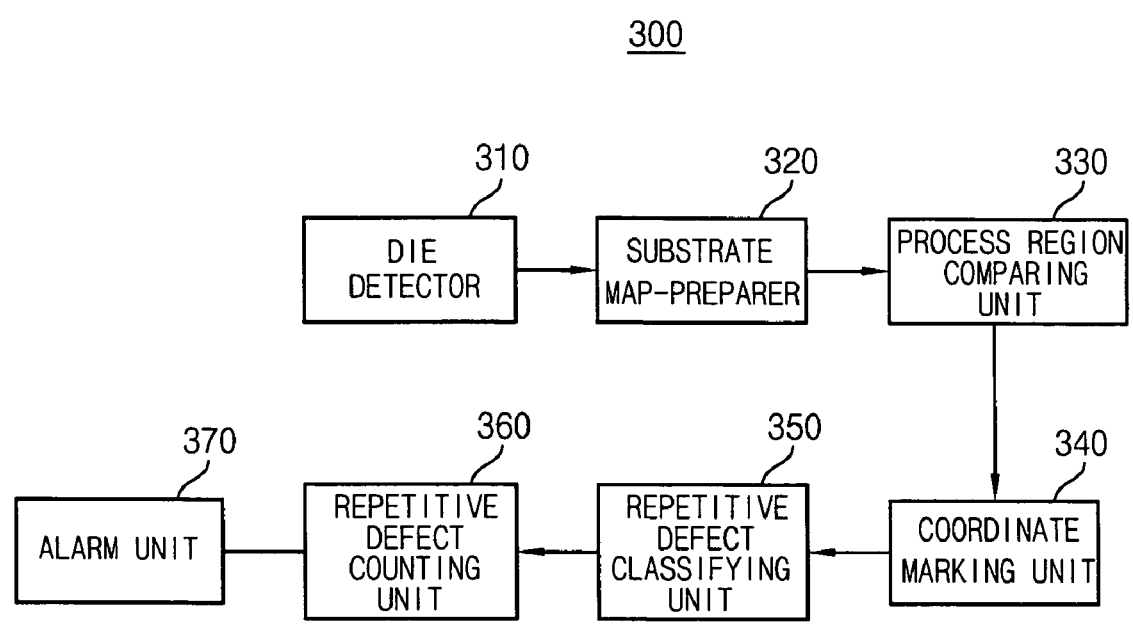
FIG. 13 is a block diagram illustrating an apparatus for classifying repetitive defects in accordance with a third embodiment of the present invention.

FIG. 13 is a block diagram illustrating an apparatus for classifying repetitive defects in accordance with a third embodiment of the present invention.

Referring to FIG. 13, an apparatus 300 for classifying repetitive defects in accordance with the present embodiment includes a defect detector 310 for detecting all of the defects on a semiconductor substrate and a map preparer 320 for preparing a map of the semiconductor substrate on which positions of all of the defects detected by the defect detector 310 are marked.

The classifying apparatus 300 includes a process region-comparing unit 330 for comparing the process regions on the substrate map with a reference process region, a coordinate-marking unit 340 for marking the positions of all of the defects on the reference process region, and a repetitive defect-classifying unit 350 for classifying repetitive defects separately from all of the other defects.

Additionally, the classifying apparatus 300 may further include a repetitive defect-counting unit 360 for counting the numbers of all of the defects and the numbers of the defects in each of the dies, and an alarm unit 370 for displaying an alarm message in accordance with the result of the count by the repetitive defect-counting unit 360.

The process region-comparing unit 330 sequentially compares the process regions on the substrate map with the reference process region.

Here, the coordinate-marking unit 340, the repetitive defect-classifying unit 350, the repetitive defect-counting unit 360 and the alarm unit 370 are substantially identical to those in Embodiment 1, respectively. Thus, any further illustrations of the coordinate-marking unit 340, the repetitive defect-classifying unit 350, the repetitive defect-counting unit 360 and the alarm unit 370 are omitted.

First, any one of processes for manufacturing a semiconductor device can be performed on each of the dies of the semiconductor substrate. An example of the process can include an exposing process. In an exposing process, a light can be irradiated onto a photoresist film on the semiconductor substrate through a reticle to form a photoresist pattern. In particular, the reticle can have twelve exposing portions so that the exposing process can be carried out on the process region including twelve dies. Thus, since all of the dies can be divided into forty-eight process regions, forty-eight exposing processes are performed.

Figure 14:
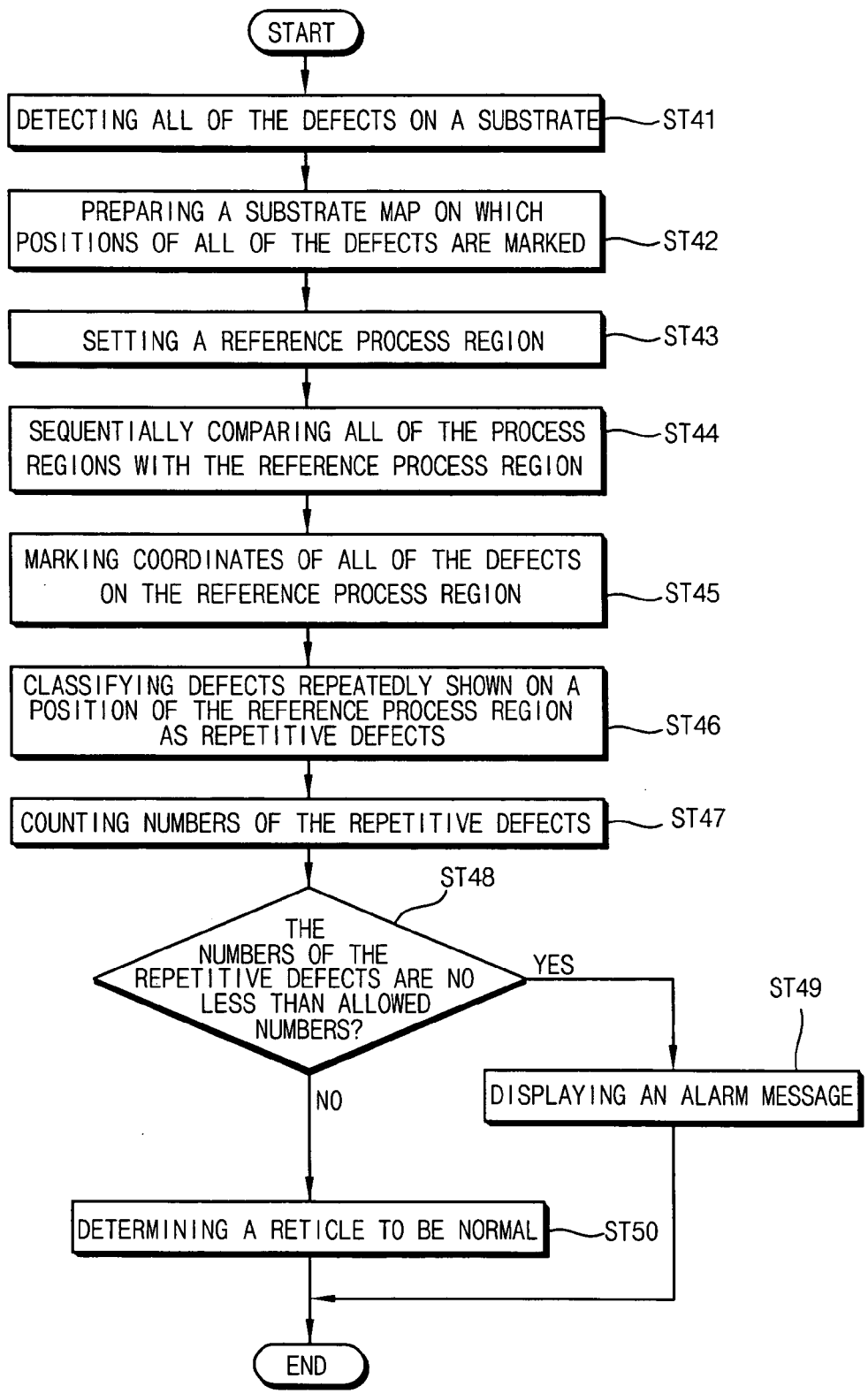
FIG. 14 is a flow chart illustrating a method of classifying repetitive defects using the apparatus in FIG. 13.

Referring to FIGS. 13 and 14, in step ST41, the defect detector 310 can detect all of the defects on the semiconductor substrate.

In step ST42, the map preparer 320 can prepare the substrate map on which all of the defects can be marked. The substrate map can be divided into a plurality of the process regions. Each of the process regions corresponds to each of the exposing portions, respectively.

In step ST43, the reference process region without defects can be set up in the process region-comparing unit 330. The reference process region can correspond to the process regions.

In step ST44, the process region-comparing unit 330 can sequentially compare each of the process regions on the substrate map with the reference process region.

In step ST45, the coordinate-marking unit 340 marks the positions of all of the defects on the X-Y coordinate system of the reference process region.

In step ST46, the repetitive defect-classifying unit 350 classifies defects repeatedly marked in the tolerance region that are set from a position on the X-Y coordinate system of the reference process region as the repetitive defects.

In step ST47, the repetitive defect-counting unit 360 counts the numbers of the repetitive defects.

In step ST48, the repetitive defect-counting unit 360 determines whether the numbers of the repetitive defects are not less than the allowed numbers.

In step ST49, when the numbers of the repetitive defects are not more than the allowed numbers, the reticle is determined to be normal.

On the contrary, in step ST50, when the numbers of the repetitive defects are not less than the allowed numbers, the alarm unit 370 displays the alarm message so that the worker recognizes the reticle to be abnormal.

Here, the alarm message may have a function for informing the worker of the existence of the repetitive defects. Alternatively, the alarm message may have an additional function for preventing the following process from being performed in order for the worker to manage the repetitive defects.

According to the present embodiment, since the process regions on the substrate map are compared with the reference process region, the repetitive defects may be accurately classified.

After all of the dies on the semiconductor substrate are compared with the reference die, all of the positions of all of the defects are set on the reference die. The defects repeatedly shown in the tolerance region of the reference die are classified as the repetitive defects. Thus, since the dies are not compared with each other, the time required for classifying the repetitive defects may be remarkably reduced compared to that of the conventional method.

Also, the positions of the dies are recognized by each of the process regions so that the repetitive defects may be accurately classified among all of the defects.

Having described the preferred embodiments of the present invention, it is noted that modifications and variations can be made by persons skilled in the art in light of the above teachings. It is therefore to be understood that changes may be made in the particular embodiment of the present invention disclosed which is within the scope and the spirit of the invention outlined by the appended claims.

What is claimed is:

1. A method for classifying repetitive defects on a substrate, comprising:
providing a die-comparing unit for sequentially comparing the dies on the substrate with a predetermined reference die;
providing a coordinate-marking unit for marking sets of coordinates on the reference die which correspond to the position of the defects on the dies on the substrate;
providing a repetitive defect-classifying unit for classifying as repetitive defects, defects corresponding to coordinates which are repeatedly marked in a reference region provided on the reference die:
sequentially comparing, using said die-comparing unit, the dies on the substrate with a predetermined reference die;
marking sets of coordinates with said coordinate-marking unit on the reference die which correspond to the position of the defects on the dies on the substrate; and
repetitively classifying with said defect-classifying unit, as repetitive defects, defects corresponding to coordinates which are repeatedly marked in a reference region provided on the reference die.

2. The method of claim 1, further comprising dividing the reference die into a plurality of classification regions that has a substantially square shape,
wherein the specified region has a cross shape including the plurality of classification regions.

3. The method of claim 1, further comprising the step of counting the number of the repetitive defects.

4. The method of claim 3, further comprising displaying an alarm message, when the number of the repetitive defects is not less than a predetermined allowed number of repetitive defects.

5. A method for classifying repetitive defects on a substrate, comprising:
providing a die-comparing unit for sequentially comparing the dies on the substrate with a predetermined reference die, the substrate being divided into process regions wherein a process is performed;
providing a coordinate-marking unit for marking sets of coordinates on the reference die which correspond to the positions of the defects on the dies on the substrate;
providing a process region-determining unit for determining whether preliminary repetitive defects are positioned in a substantially same process region;
providing a repetitive defect-classifying unit for preliminarily classifying defects corresponding to coordinates which are marked in a reference region on the reference die as preliminary repetitive defects, and for finally classifying the preliminary repetitive defects as final repetitive defects in accordance with a determination by the process region-determining unit;
sequentially comparing, using said die-comparing unit, the dies on the substrate with a predetermined reference die,
performing a process on the process regions of the divided substrate;
marking sets of coordinates on the reference die, using said coordinate-marking unit, said markings corresponding to the positions of the defects on the dies on the divided substrate;
determining with said process region-determining unit whether preliminary repetitive defects are positioned in the substantially same process region; and
using said repetitive defect-classifying unit for preliminarily classifying defects corresponding to coordinates which are marked in a reference region on the reference die as preliminary repetitive defects, and for finally classifying the preliminary repetitive defects as final repetitive defects in accordance with a determination by the process region-determining unit.

6. The method of claim 5, wherein the process regions correspond to regions that are exposed using a reticle having exposing portions and which include the dies.

7. The method of claim 5, further comprising counting the total numbers of the repetitive defects on the substrate and the number of repetitive defects on the dies.

8. The method of claim 7, further comprising displaying an alarm message, when the total numbers of the repetitive defects on the substrate are not less than a predetermined allowed number of repetitive defects.

9. The method of claim 7, further comprising displaying an alarm message, when the total numbers of the repetitive defects on the substrate are not more than a predetermined allowed numbers set by the semiconductor, and the number of the repetitive defects on the dies are not less than the predetermined allowed number set by the dies.

10. The method of claim 5, further comprising dividing the reference die into a plurality of classification regions that have a substantially square shape,
wherein the process region has a cross shape including a plurality of classification regions.

11. A method for classifying repetitive defects on a substrate, comprising:
providing a process region-comparing unit for sequentially comparing process regions on the substrate with a predetermined reference process region;
providing a coordinate-marking unit for marking coordinates on the reference process region which corresponds to the position of the defects on the process regions;
providing a repetitive defect-classifying unit for classifying defects as repetitive defects corresponding to coordinates which are repeatedly marked in a process region on the reference process region;
sequentially comparing, using said process region-comparing unit, process regions on the substrate with a predetermined reference process region;
marking coordinates, using said coordinate-marking unit, on the reference process region which corresponds to the position of the defects on the process regions; and
using a repetitive defect-classifying unit for classifying defects as repetitive defects corresponding to coordinates which are repeatedly marked in a process region on the reference process region.

12. The method of claim 11, wherein the process regions correspond to regions that are exposed using a reticle having exposing portions and including the dies.

13. The method of claim 11, further comprising dividing the reference process region into a plurality of classification regions that have a substantially square shape,
wherein the process regions have a cross shape including a plurality of classification regions.

14. The method of claim 11, further comprising counting the number of repetitive defects.

15. The method of claim 14, further comprising displaying an alarm message, when the numbers of the repetitive defects are not less than an allowed number of repetitive defects.

16. An apparatus for classifying repetitive defects on a substrate, comprising:
- a die-comparing unit for sequentially comparing the dies on the substrate with a predetermined reference die;
- a coordinate-marking unit for marking sets of coordinates on the reference die which correspond to the position of the defects on the dies on the substrate; and
- a repetitive defect-classifying unit for classifying as repetitive defects, defects corresponding to coordinates which are repeatedly marked in a reference region provided on the reference die.

17. The apparatus of claim 16, further comprising a repetitive defect-counting unit for counting the number of the repetitive defects.

18. The apparatus of claim 16, further comprising an alarm unit for displaying an alarm message when the number of the repetitive defects are not less than a determined allowed number.

19. An apparatus for classifying repetitive defects on a substrate, comprising:
- a die-comparing unit for sequentially comparing the dies on the substrate with a predetermined reference die, the substrate being divided into process regions wherein a process is performed;
- a coordinate-marking unit for marking sets of coordinates on the reference die which correspond to the positions of the defects on the dies on the substrate;
- a process region-determining unit for determining whether preliminary repetitive defects are positioned in a substantially same process region; and
- a repetitive defect-classifying unit for preliminarily classifying defects corresponding to coordinates which are marked in a reference region on the reference die as preliminary repetitive defects, and for finally classifying the preliminary repetitive defects as final repetitive defects in accordance with a determination by the process region-determining unit.

20. The apparatus of claim 19, further comprising a repetitive defect-counting unit for counting the number of the repetitive defects on the substrate and the number of repetitive defects on the dies.

21. The apparatus of claim 20, further comprising an alarm unit for displaying an alarm message when the number of the repetitive defects on the substrate are not less than allowed numbers, or when the total number of the repetitive defects on the substrate are not more than allowed numbers set by the semiconductor and the number of repetitive defects on each of the dies are not less than the predetermined allowed numbers set by the dies.

22. An apparatus for classifying repetitive defects on a substrate, comprising:
- a process region-comparing unit for sequentially comparing process regions on the substrate with a predetermined reference process region;
- a coordinate-marking unit for marking coordinates on the reference process region which corresponds to the position of the defects on the process regions; and
- a repetitive defect-classifying unit for classifying defects as repetitive defects corresponding to coordinates which are repeatedly marked in a process region on the reference process region.

23. The apparatus of claim 22, further comprising a repetitive defect-counting unit for counting the number of the repetitive defects.

24. The apparatus of claim 23, further comprising an alarm unit for displaying an alarm message when the number of the repetitive defects are not less than a predetermined allowed number.

25. A method of classifying repetitive defects on a substrate, comprising:
- sequentially comparing defects of dies on the substrate with a predetermined reference die;
- dividing the substrate into process regions wherein a process is performed;
- marking sets of coordinates on the reference die which are corresponding to the position of the defects on the dies on the substrate;
- classifying defects as preliminary repetitive defects which correspond to coordinates which are repeatedly marked in a process region on the reference die;
- determining whether the preliminary repetitive defects are positioned in substantially the same process region;
- classifying the preliminary repetitive defects within substantially the same process region as final repetitive defects;
- counting the total numbers of the repetitive defects on the substrate and the number of repetitive defects on the dies; and
- displaying an alarm message, when the total numbers of the repetitive defects on the substrate are not more than a predetermined allowed numbers set by the semiconductor, and the number of the repetitive defects on the dies are not less than the predetermined allowed number set by the dies.

* * * * *

UNITED STATES PATENT AND TRADEMARK OFFICE
CERTIFICATE OF CORRECTION

PATENT NO. : 7,339,663 B2 Page 1 of 1
APPLICATION NO. : 11/181162
DATED : March 4, 2008
INVENTOR(S) : Young-Kyu Lim et al.

It is certified that error appears in the above-identified patent and that said Letters Patent is hereby corrected as shown below:

Column 13, line 17, the word "die:" should read -- die; --;
Column 14, line 19, the word "dcfects" should read -- defects --;
Column 16, line 3, the word "numbcrs" should read -- number --.

Signed and Sealed this

Nineteenth Day of August, 2008

JON W. DUDAS
*Director of the United States Patent and Trademark Office*